United States Patent

Kley et al.

[11] Patent Number: 5,098,848
[45] Date of Patent: Mar. 24, 1992

[54] METHOD AND APPARATUS FOR MEASURING THE AIR CONTENT OF WATER-SOLUBLE OXIDIZERS

[75] Inventors: Dieter Kley; Stefan Gilge, both of Jülich; Jelena Jeftic, Zagreb; Andreas Volz-Thomas, Erkelenz-Hetzerath, all of Fed. Rep. of Germany

[73] Assignee: Forschungszentrum Jülich GmbH, Postfach Jülich, Fed. Rep. of Germany

[21] Appl. No.: 581,276

[22] Filed: Sep. 12, 1990

[30] Foreign Application Priority Data

Sep. 19, 1989 [DE] Fed. Rep. of Germany ....... 3931193

[51] Int. Cl.$^5$ ............................................. G01N 27/00
[52] U.S. Cl. ..................... 436/150; 436/124; 436/125; 436/151
[58] Field of Search ............... 436/134, 125, 124, 150, 436/151, 178; 73/31.07, 23.2

[56] References Cited

U.S. PATENT DOCUMENTS

| | | | |
|---|---|---|---|
| 1,375,933 | 4/1921 | Rideal et al. | 436/134 |
| 3,871,827 | 3/1975 | Seilee et al. | 436/134 |
| 3,880,722 | 4/1975 | Beltzer | 436/134 |
| 4,145,913 | 3/1979 | Brown et al. | 73/31.07 |

Primary Examiner—Robert J. Hill, Jr.
Assistant Examiner—Newton Edwards
Attorney, Agent, or Firm—Frishauf, Holtz, Goodman & Woodward

[57] ABSTRACT

Air containing water-soluble oxidizing agents, usually predominantly hydrogen peroxide, is exposed in concurrent flow to water that may be acidified if the air contains interfering acidic reducing agents such as sulfur dioxide. After that exposure the gas is separated from the liquid and, if the stripping liquid has been acidified, it is then neutralized. The neutral stripping liquid containing the oxidizing agents is mixed and then reacted with an iodide solution in the presence of a catalyst, after which the reaction products are passed, as the cathode solution, through an electrochemical concentration cell which has an anode chamber filled with a concentrated iodide solution as an anode solution. The volume of air exposed to the stripping liquid is continuously measured and likewise, in the concentration cell, the iodine formed before the mixed solution enters the concentration cell is continuously measured, so that content of water-soluble oxidizing agents in the air can be continuously measured or monitored.

4 Claims, 1 Drawing Sheet

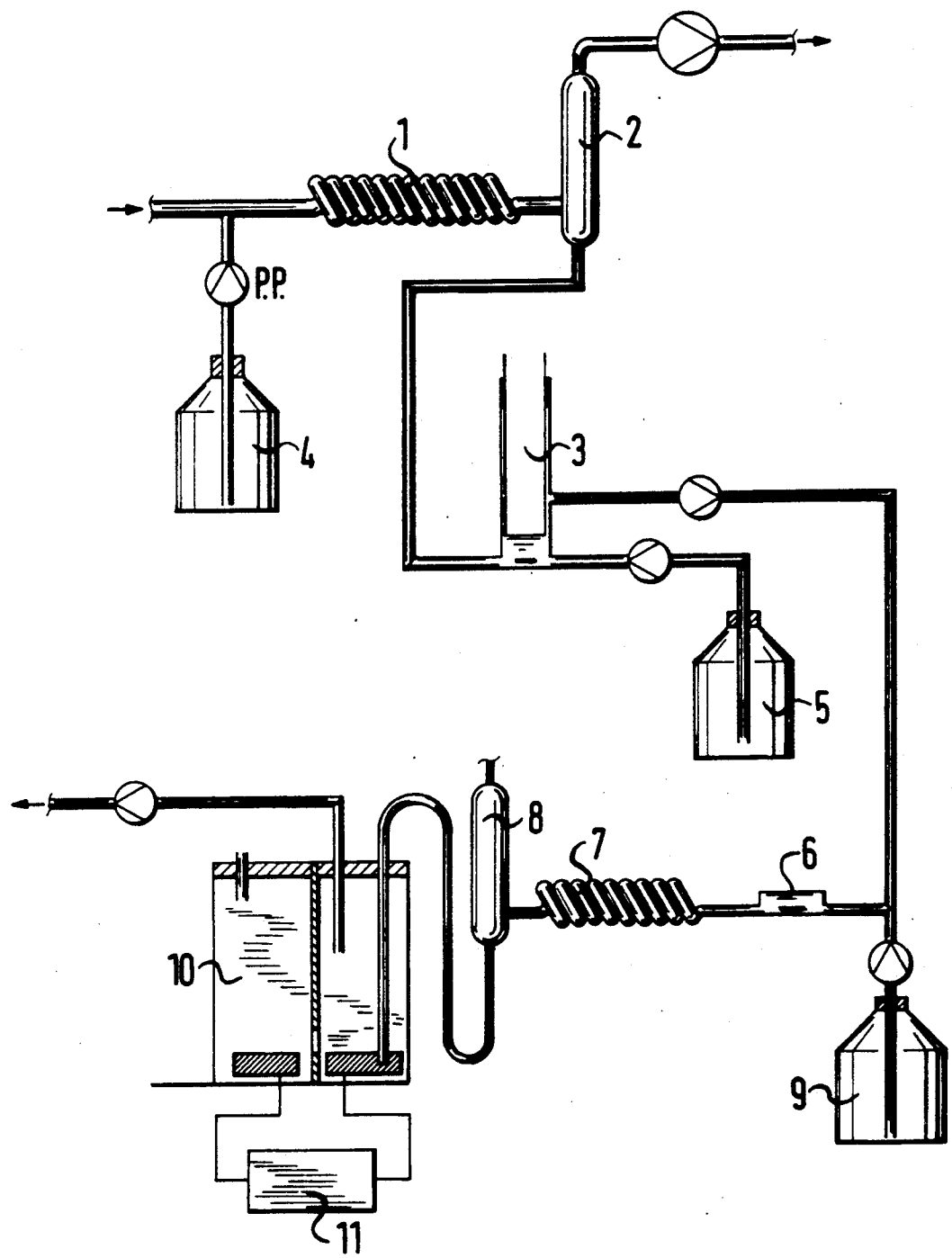

METHOD AND APPARATUS FOR MEASURING THE AIR CONTENT OF WATER-SOLUBLE OXIDIZERS

This invention concerns a method for detecting and measuring the content of water-soluble oxidizers in air, and more particularly a method in which the air quantity to be analyzed is guided past a stripper liquid for absorption or other removal of the oxidizers, especially $H_2O_2$. The apparatus of the invention includes a first stage which guides the air to be analyzed over a stripper liquid in which the oxidizers are absorbed Analysis of trace elements and compounds in the atmosphere is of increasing interest and significance, because of air pollution which is becoming steadily more problematic. The investigations are directed also to the presence of water-soluble oxidizers in the air. The most important component of these oxidizers is hydrogen peroxide, which is found in higher concentrations than the other water-soluble oxidizers, so that the measurement of the content of such oxidizers in practice concerns essentially a determination of the hydrogen peroxide content.

In order to be able to measure and monitor substances in the atmosphere which are present only in trace quantities, it is not enough for the measuring processes to be sufficiently precise. More importantly, in order to make possible economic installations or devices, for example in vehicles used for the measurements, the methods must be simple or performable with simple apparatus. This is particularly important in a variety of cases, including investigations of the upper levels of the atmosphere, where it is desirable to use apparatus in the form of a balloon-carried probe.

The heretofore known measuring methods for determining the content of oxidizers in the atmosphere require relatively complicated and heavy apparatus and are therefore suited only for ground installations and, for mobility, only in airplanes.

SUMMARY OF THE INVENTION.

It is an object of the present invention to provide a measuring method and apparatus for determining the water-soluble oxidizer content of air which is simple and nevertheless sufficiently accurate in which a simple and economic apparatus can be used to produce the results. A provision of such apparatus is a further object of the invention.

Briefly, the stripper liquid containing the oxidizers is mixed with a liquid containing an iodide, in which the oxidizers, in the presence of a catalyst that is provided, react with the iodide to produce iodine ($I_2$). The solution containing the reaction products is then supplied to an electrochemical concentraction cell operated in through-flow, in which the continuously removed and renewed solution containing the reaction products is the cathode solution and a concentrated iodide solution is the anode solution. The concentration of oxidizers is determined and indicated by means of the quantity of generated iodine with reference to the quantity of air which has been subjected to analysis.

When the air is passed over a body of stripper liquid in a known way, for example utilizing a collecting helix, the water soluble oxidizers can be practically completely absorbed (up to 99%) by the liquid if the collecting helix is suitably dimensioned. The water-soluble oxidizers are separated in this process from other oxidizers not soluble in water, for example by use of a gas separator. Thus, for example, ozone, that surely constitutes the largest content of oxidizing trace gases in the atmosphere, is only negligibly absorbed in a stripping liquid, as shown in the following example.

EXAMPLE 1

With air having an $H_2O_2$ concentration of 1 ppb, the application of a suction power of 6 liters per minute and a stripper flow of $5.7 \times 10^{-4}$ liters per minute, there is obtained, with almost 100% collecting efficiency, an $H_2O_2$ concentration in the stripper liquid of:

$$(6\ l/min/22.4\ l/mol) \times 10^{-9} \times 1.75 \times 10^3$$
$$min/l = 4.7 \times 10^{-7}\ mol/l.$$

In contrast thereto, even at comparably high ozone concentrations of 100 ppb and maximum enrichment (at an equilibrium with a Henry constant of $H = 1.1 \times 10^{-2}$ mol/l), there is obtained only a concentration of:

$$100 \times 10^{-9}\ bar \times 1.1 \times 10^{-2}\ mol \times l^{-1}$$
$$bar^{-1} = 1.1 \times 10^{-9}\ mol/l$$

i.e. only about 0.2% of the measurement value is the result of ozone.

Interference by disturbing reducing agents must likewise be excluded. Insofar as these agents are insoluble or only poorly soluble, their effects are avoided as above by separation. Sulfur dioxide, however, as the most important example of interfering reducing agents, has good solubility in neutral solutions. If the stripper solution is acidified, the solubility of sulfur dioxide is indeed less, but the side reaction of already collected $H_2O_2$ with $SO_2$ in the stripper helix becomes very rapid, so that $SO_2$ is continuously reacted away and can be absorbed anew from the air. Only at pH values smaller than 1 can this reaction be kept slow. In the case in which the $SO_2$ concentration exceeds the concentration of $H_2O_2$ which is to be expected, a 1-normal strength acid is used as the stripper liquid instead of water, i.e. a stripper liquid acidified to a pH value of at least 0.1 is used. It is neutralized after the collection of the oxidizers, but before the mixture with the liquid containing the iodide.

In order to be able to carry out the process on a reasonable time scale, transition metal complexes are advantageously used as catalysts which sufficiently accelerate the reaction $H_2O_2 + I^{3l} \rightarrow I_2$. Such metal complexes are salts of Mo (VI), Fe (III), Zr (IV), W (VI), Ce (III), Hf (IV), V (IV), V (V), Nb (V), Ta (V), Ru (IV), Ru (III), Os (VIII) and Ti (IV). Among these molybdenum-VI salts have been found to be particularly suitable for use as catalysts for the oxidation of iodine ions.

For determining the amount of iodine generated in the reaction, a concentration cell operated in through-flow is advantageously used. The reaction products contained in the solution function as the cathode solution. This solution is about 0.05 molar as iodide. The anode solution is conveniently a concentrated or saturated potassium iodide solution which has about an 8.0 molar content of iodide. At first an equilibrium is produced between the cathode and anode spaces, i.e. before the measurement, which is determined by the concentration ratio of iodide to iodine. If then during the performance of the measuring process a reaction mixture containing iodine is supplied to the cathode space, the initial equilibrium is changed and an electric current flows until the equilibrium is again established. This current is directly proportional to the iodine or to the oxidized amount of iodide and therefore to the concentration of oxidizers The measurement of the current is conveniently performed with an electrometer The measured current lies in the range from a few $10^{-8}$ ampere (null current) up to $10^{-5}$ ampere (signal), so that the measurement method is uncritical. The current data can of course be supplied to a computer and further processed.

In the apparatus of the invention, three stages are used in sequence and make it possible to operate the process in a continuous through-flow.

BRIEF DESCRIPTION OF THE DRAWING.

The apparatus of the invention is further described with reference to the annexed drawing, the single FIGURE of which is a schematic representation of the apparatus, in side view.

DESCRIPTION OF THE ILLUSTRATED EMBODIMENT.

The first stage of the apparatus comprises an air-flow measuring device 12, a collecting helix 1, a gas separator 2 which follows the collecting helix and a stirring cell 3, as well as the vessels 4 and 5 connected, as shown in the drawing, respectively at the beginning and at the end of the first stage.

The air to be analyzed, in a volume continuously measured at 12, passes through the collecting helix 1 where it is exposed to the stripper liquid which is supplied into the helix 1 from the vessel 4. While the air then passes through the gas separator 2 to the exhaust air discharge at the top of the gas separator 2, the stripper liquid, enriched by the oxidizing agents which are to be measured, flows into the stirring cell 3, in which, if that should be necessary, it can be neutralized with a neutralization solution provided from the vessel 5. A glass electrode (not shown) can be inserted into the stirring cell 3, if that should be desired for the measurement of the pH value of the liquid or for checking the pH value.

The second stage of the apparatus comprises the mixing cell 6, the reaction helix 7 and the second gas separator 8 which follows the reaction helix. It also includes the vessel 9, which supplies the iodine-containing solution which is mixed with the liquid coming out of the mixing cell 3 of the first stage.

After mixing with the iodide solution, the liquid from the first stage flows through the mixing cell 6 and into the reaction helix 7. After it leaves the reaction cell gas bubbles still present are separated in the gas separator 8. These gas bubbles are purposely carried along up to that point in order to separate the solution in the reaction helix and thereby to prevent impoverishment of the solution by back diffusion.

The third stage comprises the electrochemical concentration cell 10 which is equipped with two platinum electrodes respectively dipping into the solutions in the cathode and anode chambers and is connected to an electrometer 11. The electrometer measurement is correlated with the air volume measurement from the flowmeter 12 in a unit 13 to obtain a measurement of the concentration of water-soluble oxidizers in the analyzed air.

All of the liquids are furnished through peristaltic pumps, as designated in the drawing by the designation P.P. of the pump between the vessel 4 and the input side of the spiral 1. The quantity of liquid feed can be optimized by the adjustment of the rotary speed of the pump, the diameter of the flexible tubes and the applied pressure.

The method of the invention can be performed with the apparatus above described in accordance with the following example.

EXAMPLE 2

(a) Collection Process (first stage)

With a flow of air having an $H_2O_2$ concentration of 1 ppb, propelled by a suction power of 6 liters per minute and with a stripper flow of $5.7 \times 10^{-4}$ liters per minute there is obtained an $H_2O_2$ concentration in the stripper solution of $(6 \text{ lmin}^{-1}/22.4 \text{ 1} \times \text{mol}^{-1}) \times 10^{-9} \times 1.75 \times 10^3$
$\text{min}/1 = 4.7 \times 10^{-7}$
$\text{mol} \times 1^{-1}$ For the case in which there is present a concentration of $SO_2$ of 10 ppb in the air to be analyzed, the following data resulted:

1 ppb $H_2O_2$; 10 ppb $SO_2$; pH=0.1

$SO_2$ concentration in solution: $[S_{(IV)}]_{sol} = H_{S(IV)} \times [SO_2]_{air}$ in which $H_{S(IV)} = H_{SO_2} (1 + K_1/[H^+] + K_1 \times K_2/[H^+]^2)$ $K_1 = 1.74 \times 10^{-2}$ mol/l $K_2 = 6.24 \times 10^{-8}$ mol/l $H_{SO_2} = 1.24$ mol/l $\times$ bar $\rightarrow [S_{(IV)}]_{1sg} = 1.24$ mol/l $\times$ bar $10 \times 10^{-9}$ bar $= 1.3 \cdot 10^{-8}$ mol/l side reaction $d (S_{(IV)})/dt =$ $8.3 \times 10^4 [H_2O_2][SO_2 \, aq] (0.1 + [H^+])^{-1}$
(for pH 0-2)

$H_2O_2$-concentration: as above $(4.7 \times 10^{-7}$ mol/l)

$\rightarrow d (S_{(IV)})/dt = 5.41 \times 10^{-10}$ mol/l $\times$ sec standing time of solution in helix: 20.8 seconds $[S_{(IV)}]$side-reac $= 1.1 \times 10^{-8}$ mol/l altogether $2.4 \times 10^{-8}$ mol/l $S_{(IV)}$ in solution.

The above signifies that about 5% of the $H_2O_2$ quantity has been removed from the results by $SO_2$.

The gaseous and the liquid phases are then separated from each other in the gas separator 2.

(b) Chemical Conversion.

In the mixing cell 6, the stripper liquid loaded with $H_2O_2$ is mixed with the so-called conditioning solution, which consists of potassium iodide (KI), disodium hydrogen phosphate ($Na_2HPO_4 \cdot 12 \, H_2O$) and ammonium heptamolybdate (($NH_4)_6Mo_7O_{24} \cdot 4 \, H_2O$) in particular concentration ratios (e.g.: KI 0.48 mol/l; $Na_2HPO_4$ 0.11 mol/l; $(NH_4)_6Mo_7O_{24}$ 6.5 $\times 10^{-3}$ mol/l), all of these being dissolved in water.

In the reaction helix 7 the $H_2O_2$ reacts completely and quantitatively with the KI to produce $I_2$. In that reaction the ammonium heptamolybdate acts as a catalyst by substantially shortening the reaction time. Probably $H_2O_2$ molecules and $I^-$ ions enter into the ligand sphere of the molybdenum and there react intramolecularly.

(c) Electrochemical Results.

The solution containing the reaction products is fed into the cell 10 as cathode solution. It has about 0.05 molar content of iodide. The anode solution has about 8.0 molar content of potassium iodide The two chambers are connected to each other by a salt bridge. The electromotive force (EMF) that results is determined by the concentration ratio of iodide to iodine:

$$EMF = -0.059/2 \times \log (a_1)I_3^- \times (a_3)^2 I^- \times [(a_4)I_2 \times (a_2)^3 I^-]^{-1}$$

$a_1$ and $a_2$ are the activities of the $I_2$ (or $I_3^-$) and $I^-$ ion concentrations in the anode chamber; $a_3$ and $a_4$ those of the $I^-$ and $I_2$ concentrations in the cathode chamber. If now the two electrodes are connected, for example through the electrometer 11, a current flows and the mutually corresponding activities change until the equilibrium condition set forth below is fulfilled:

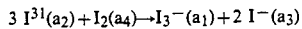

The cell operates in this equilibrium. If now the ratio of $I^-$ to $I_2$ changes in favor of the $I_2$ the value /beta/ becomes less than 1 and a measurable electric current flows, because the cell operates to restore the equilibrium according to:

$$3\,I^{31}(a_2) + I_2(a_4) \rightarrow I_3^-(a_1) + 2\,I^-(a_3)$$

This current is directly proportional to the oxidized quantity of iodide and thereby also to the hydrogen peroxide concentration Up to now an accuracy of about 0.1 ppb and a solution time of about 2 minutes has been obtained with the measuring method.

The method measures the sum of the water-soluble oxidizing agents and accordingly does not distinguish between $H_2O_2$ and organic peroxides. Since the organic peroxides occur mostly in substantially smaller concentrations compared to $H_2O_2$, the absence of this distinction is not significant for the interpretation of the data.

Although the method and apparatus of the invention has been disclosed with reference to particular examples, it will be understood that modifications and variations are possible within the inventive concept.

We claim:

1. A method of measuring the water-soluble oxidizers contained in air in which air to be analyzed is exposed in concurrent flow to the affect of an aqueous stripper liquid, from which gas is thereafter separated, said method comprising the steps of:
   after the exposure of the air to the aqueous stripper liquid and the separation of gas therefrom, mixing the stripper liquid containing the oxidizers with a liquid containing an iodide;
   reacting the stripper liquid and the iodide-containing liquid together in the presence of a catalyst to produce iodine in solution;
   thereafter passing the solution containing the iodine and other reaction products into a flow-through electrochemical concentration cell having a flow-through cathode chamber and an anode chamber, in which chambers electrodes are respectively provided, a concentrated ioide solution being provided in said anode chamber, while continuously producing an electrical measurement, representative of the amount of iodine produced by said reaction in a circuit in which said electrodes participate;
   continuously measuring, concurrently, the quantity of air exposed to said stripper liquid, and
   continuously determining the oxidizing agent concentration in air with reference both to said electrical measurement and to said measurement of the quantity of air exposed to said stripper liquid.

2. The method of claim 1, wherein said aqueous stripper liquid is a liquid acidified to a pH value of at least 0.1 and wherein after exposure of said air to said stripper liquid the separation of gas from the liquid, but before mixing with a liquid-containing iodide, said stripper liquid is neutralized.

3. The method of claim 1, wherein a molybdenum VI salt is included in said catalyst to said iodide-containing liquid which is mixed with said stripper liquid or reaction between them.

4. The method of claim 2, wherein a molybdenum VI salt is included in said catalyst to said iodide-containing liquid which is mixed with said stripper liquid or reaction between them.

* * * * *